(12) United States Patent
Stec

(10) Patent No.: US 10,159,598 B2
(45) Date of Patent: Dec. 25, 2018

(54) UNDERBODY CONVECTIVE BLANKET

(71) Applicant: SMITHS MEDICAL ASD, INC., Rockland, MA (US)

(72) Inventor: Alan E. Stec, East Bridgewater, MA (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 1007 days.

(21) Appl. No.: 14/160,682

(22) Filed: Jan. 22, 2014

(65) Prior Publication Data

US 2014/0214141 A1 Jul. 31, 2014

Related U.S. Application Data

(60) Provisional application No. 61/757,808, filed on Jan. 29, 2013.

(51) Int. Cl.
*A61F 7/00* (2006.01)

(52) U.S. Cl.
CPC ...... *A61F 7/0097* (2013.01); *A61F 2007/006* (2013.01); *A61F 2007/0091* (2013.01); *A61F 2007/0098* (2013.01); *Y10T 29/49826* (2015.01)

(58) Field of Classification Search
CPC .......................................................... A61F 7/02
See application file for complete search history.

(56) References Cited

U.S. PATENT DOCUMENTS

| 4,461,048 | A | * | 7/1984 | Allaire, Jr. | ........... | A47G 9/0246 |
| | | | | | | 5/493 |
| 5,125,238 | A | | 6/1992 | Ragan et al. | | |
| 5,165,400 | A | * | 11/1992 | Berke | ........................ | A61F 7/00 |
| | | | | | | 5/482 |
| 5,749,109 | A | | 5/1998 | Kappel | | |
| 2005/0125048 | A1 | | 6/2005 | Paolini et al. | | |
| 2006/0052851 | A1 | * | 3/2006 | Anderson | .............. | A61F 7/0097 |
| | | | | | | 607/104 |
| 2009/0248120 | A1 | | 10/2009 | Starr et al. | | |
| 2010/0211139 | A1 | * | 8/2010 | Pierre | .................... | A61F 7/0097 |
| | | | | | | 607/104 |
| 2012/0253435 | A1 | | 10/2012 | Pierre et al. | | |

FOREIGN PATENT DOCUMENTS

JP 11-513279 11/1999

OTHER PUBLICATIONS

PCT International Search Report and Written Opinion, dated May 9, 2014, issued in related PCT Application No. PCT/US2014/021432, by the ISA in Korea.

* cited by examiner

*Primary Examiner* — Luther G Behringer
(74) *Attorney, Agent, or Firm* — Louis Woo

(57) ABSTRACT

A full body convective blanket has a head portion, a body portion and a foot portion. The head and foot portions each taper in a decreasing manner from a corresponding opposite side of the body portion to the head and foot ends, respectively, so that the blanket has a rectangular shaped body portion and head and foot portions that are shaped in the form of isosceles trapezoids. Two elongate openings are provided longitudinally along the body portion sandwiching a non-inflatable area. An opening is provided at the head portion of the blanket.

8 Claims, 3 Drawing Sheets

UNDERBODY CONVECTIVE BLANKET

FIELD OF THE INVENTION

The present invention relates to convective warming blankets and more particularly to an underbody blanket configured for enhanced airflow distribution and has openings where through the arms of the patient may be extended

BACKGROUND OF THE INVENTION

Full size underbody blankets are known. One such is disclosed in US publication 2006/0052851 and its divisional publication US 2011/0098794. The '851 publication discloses a full size underbody blanket that has two longitudinal seals with perforations therealong that enable those seals to be opened so that the arms of the patient may be extended there through. The problem with such a scheme is that there are times that it may be difficult to tear the elongate seals since a patient is lying thereon. Also, the placement of the blanket onto the surgical bed may require the pulling of the blanket along the surgical bed. This may cause the tearing of the seals and thus may affect the handling of the blanket.

SUMMARY OF THE PRESENT INVENTION

The blanket of the instant invention is a full size convective underbody blanket that has a head portion, a body portion and a foot portion. The body portion is substantially rectangular in shape. The head and foot portions each extend from an opposite presumptive side end of the body portion in a decreasing tapered manner so that each of the head and foot portions has a shape in the form of an isosceles trapezoid. The bases of the isosceles trapezoidal head and foot portions are the corresponding side ends of the body portion from which those portions extend, while the top of the head and foot portions are the head and foot ends, respectively, of the blanket that are parallel to the side ends of the body portion. There are two elongate openings, each defined by a non-ending seal, extending substantially along the length of the body portion. The two elongate openings sandwich a non-inflatable area whereonto a major part of the body of the patient lies when the patient is placed onto the blanket. At the head portion, there is a head area defined by another non-ending seal that encircles an opening that may have a substantially rectangular oval shape. Apertures are provided at selective portions of the upper sheet proximate to the head area. There are also respective rows of apertures provided in the upper sheet of the blanket substantially along the length of the body portion between the non-inflatable area and each of the elongate openings. Heated air is input to the blanket via either one of two available air inlet ports. The foot portion has multiple apertures selectively punched in the upper sheet of the blanket to effect a pressure drop thereat to increase the circulation of airflow in the blanket.

There are two tuck flaps attached to the underside of the blanket. Each tuck flap has one of its longitudinal edges fixedly attached substantially along the longitudinal edge of a corresponding one of the elongate openings. Although not necessary, to improve the folding and movability of the blanket, the side edges of each tuck flap that are orthogonal to the tuck flap's longitudinal edges may be non-removably attached to the underside of the blanket beyond the two ends of the elongate opening associated with the tuck flap, so as to be in intimate contact therewith. The longitudinal portion of each of the tuck flaps not fixedly attached to the underside of the blanket extends away from the peripheral edge of the blanket. Thus, the tuck flaps may act as supports for the blanket and the exposed longitudinal portions of the tuck flaps may be used to manipulate the blanket on its resting platform, even with the patient lying on the blanket, if it is necessary to reposition the blanket relative to the patient and/or the surgical table, or the support platform onto which the blanket is positioned. After final positioning of the blanket, the orthogonal side edges of the tuck flaps may be removed from the underside of the blanket. The freely hanging tuck flaps may then be used to secure the blanket to the surgical table, or other support platform onto which the blanket lies.

The present invention is therefore directed to an underbody blanket that comprises an air impermeable upper sheet and an air impermeable lower sheet bonded to each other at their respective peripheries to form an inflatable structure having a periphery defining therewithin a head portion, a body portion and a foot portion, both longitudinal sides of each of the head and foot portions narrowing in a tapered manner toward each other from opposite sides of the body portion to respective head and foot ends of the structure to establish a configuration for the structure that facilitates an evenly distributed airflow inside the structure. The blanket of the instant invention further comprises two elongate openings each defined by a non-ending seal extending longitudinally along the blanket substantially along the length of the body portion, the elongate openings sandwiching a non-inflatable area of the body portion whereon the body of the patient rests when the patient is positioned onto the upper sheet of the blanket; at least one inlet port provided in the structure; and apertures formed in the upper sheet to enable heated air input via the inlet port to inflate the structure to escape. Respective rows of apertures are provided along each longitudinal side of the non-inflatable body area, and are configured to be positioned to the face the patient when the structure is inflated so that heated air output from the respective rows of apertures is directed to the patient.

The instant invention is further directed to a convective blanket that comprises: an air impermeable upper sheet and an air impermeable lower sheet bonded together at their respective peripheries to form an inflatable structure having a substantially rectangular body portion, a head portion extending from one side of the body portion in a decreasing tapered manner to a head end of the blanket and a foot portion extending from other side of the body portion in a decreasing tapered manner to a foot end of the blanket so that the head and foot ends of the blanket each have a smaller width than the width across the body portion, the body portion having a non-inflatable area. The blanket further comprises two elongate openings extending along substantially the length of the body portion, the elongate openings sandwiching the non-inflatable area; at least one inlet port to enable heated air to be input into the structure to inflate the blanket; and respective rows of apertures provided along the body portion between each of the elongate openings and the non-inflatable body area positioned to face the patient when the blanket is inflated so that the heated air output from those respective rows of apertures is directed toward the non-inflatable area.

The instant invention is moreover directed to a method of manufacturing a convective blanket that comprises the steps of:

(a) bonding an air impermeable upper sheet and an air impermeable lower sheet together at their respective peripheries to form an inflatable structure having a substantially rectangular body portion, a head portion extending in a decreasing tapered manner from one side of the body portion to a head end and a foot portion extending in a decreasing tapered manner from the other side of the body portion to the foot end of the structure so that the head and foot ends of the blanket each have a smaller width than the width across the body portion, the body portion having a non-inflatable area;

(b) extending two elongate openings along substantially the length of the body portion, the elongate openings sandwiching the non-inflatable area;

(c) providing at least one inlet port to enable heated air to be input into the structure to inflate the blanket; and (d) providing respective rows of apertures along the body portion between each of the elongate openings and the non-inflatable body area positioned to face the patient when the blanket is inflated so that the heated air output from those respective rows of apertures is directed toward the non-inflatable area.

BRIEF DESCRIPTION OF THE FIGURES

The present invention will become apparent and the invention itself will be best understood with reference to the following description of the present invention taken in conjunction with the accompanying drawings, wherein.

DETAILED DESCRIPTION OF THE INVENTION

Figure 1:
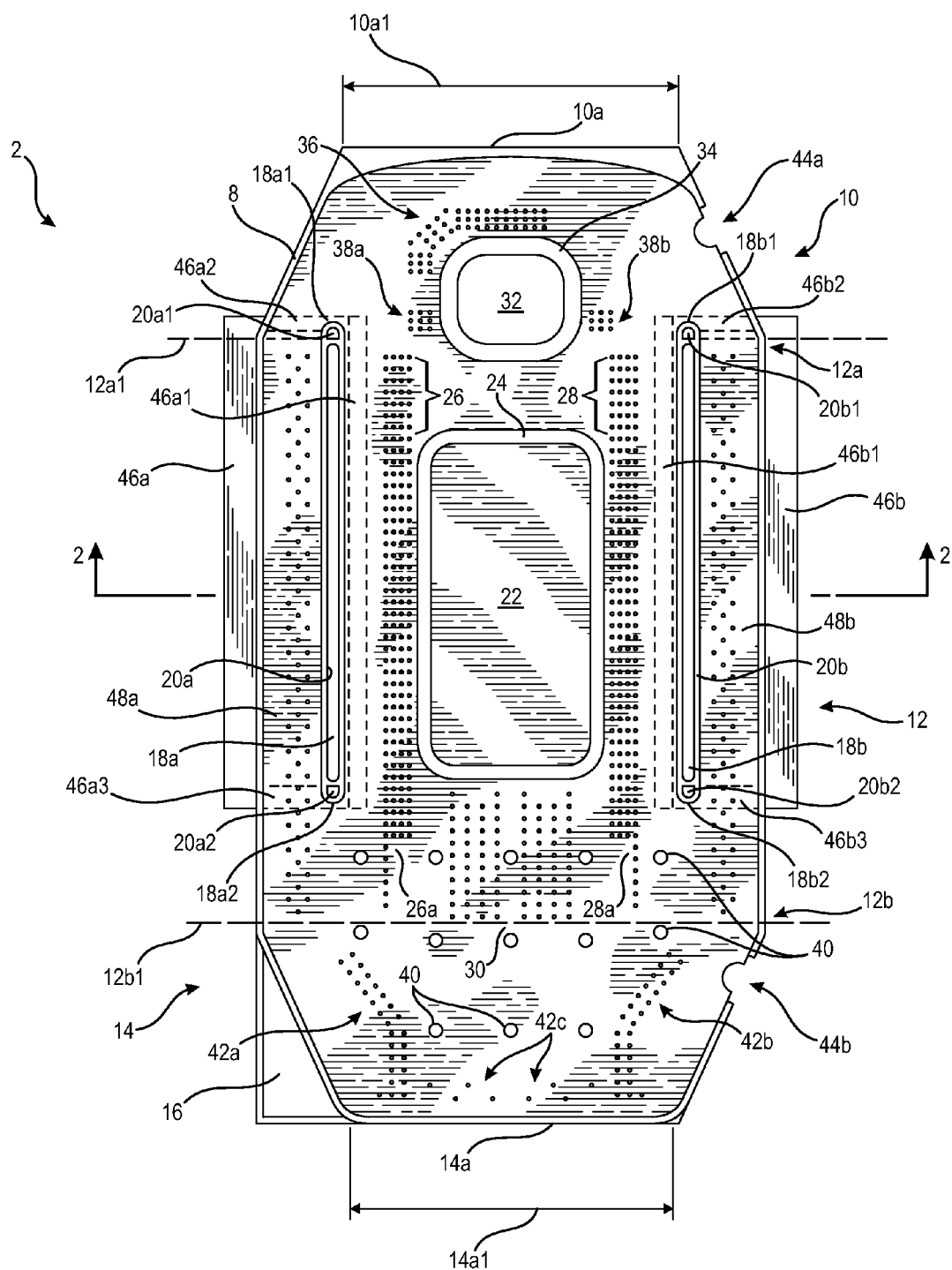
FIG. 1 is a plan view of the blanket of the instant invention.
Figure 2:
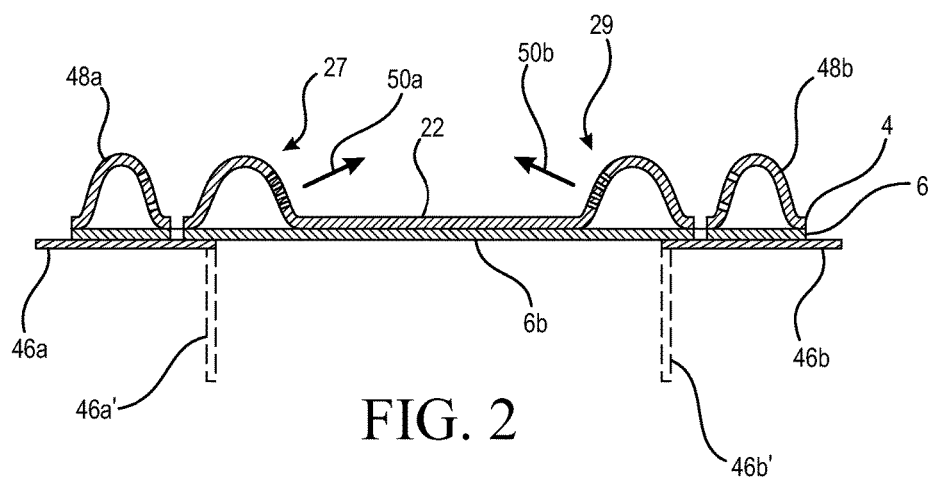
FIG. 2 is a cross-sectional view of the blanket of FIG. 1.

With reference to FIGS. 1 and 2, the instant invention blanket 2 is a convective blanket comprising an upper sheet or layer 4 and a lower sheet or layer 6 bonded to each other at their respective peripheries 8 to form an inflatable structure. Within periphery 8 there are a head portion 10, a body portion 12 and a foot portion 14. Body portion 12 has a substantially rectangular shape extending longitudinally along the blanket with two opposite sides that are presumed to be the corresponding junctions or presumptive side ends 12a and 12b where the body portion 12 meet or merge with the head and foot portions 10 and 14, respectively.

The head portion 10 is shown to extend in a narrowing or decreasing tapered manner from side end 12a of body portion 12 to head end 10a of the blanket. Similarly, the foot portion 14 is shown to extend in a decreasing tapered manner from opposite side end 12b of body portion 12 to foot end 14a of the blanket. Thus, each of head portion 10 and foot portion 14 of the exemplar blanket has the shape of an isosceles trapezoid. The parallel sides of the isosceles trapezoidal head portion are the side end 12a, represented by dotted line 12a1, and head end 10a; while the parallel sides of the isosceles trapezoidal foot portion are the side end 12b, represented by the and 12b1, and the foot end 14a. Being isosceles trapezoids, the respective tapered sides of both the head and foot portions have the same length. Thus constructed, blanket 2 has a structure whose interior space (aside from the flow channels to be discussed below) is substantially continuous and devoid of sharp angles or curves. Accordingly, blanket 2 promotes even distribution of air flow within the blanket.

As discussed above, blanket 2 is sealed at its periphery 8. There is however a self contained sealed non-inflatable area 16 at the foot portion 14 of the blanket. Area 16 provides an indication to the user of where the foot portion 14 of the blanket is so that the user does not have to guess at the orientation of the blanket, when the blanket is first removed from its packaging. Area 16 may also be a place on the blanket where information, such as writings or symbols relating to the blanket, may be presented to the user.

Two elongate openings 18a and 18b extend along substantially the length of the body portion of the blanket 2, with their respective first ends 18a1 and 18b1 partially extending into the head portion 8. Elongate openings 18a and 18b are formed by respective non-ending seals 20a and 20b. Each of the non-ending seals 20a and 20b has at its respective ends a sealed cavity to provide strain relief for the elongate openings. Thus, sealed cavity 20a1 is provided at end 18a1 while sealed cavity 20a2 is provided at end 18a2 for seal 20a. Similarly, a sealed cavity 20b1 is provided at end 18b1 and a sealed cavity 20b2 is provided at end 18b2 for seal 20b. The strain relief to both ends of each of elongate openings 18a and 18b enhances the integrity of the openings and ensures that even were the openings to be stretched, the ends of the opening would in most instances not tear or extend beyond what is shown in FIG. 1. For the exemplar blanket shown in FIG. 1, the length of each of the elongate openings 18a and 18b may be from approximately 30 inches to 40 inches (76 cm to 102 cm), and preferably between 32-37 inches (81-94 cm). The width of the elongate openings may be anywhere from approximately ¼-1½ inches (0.64-3.80 cm).

Within the body portion 12 there is a non-inflatable body area 22 formed or defined by a non-ending seal 24. A number of rows of apertures 26 and 28 are provided longitudinally at the upper sheet 4 adjacent to and beyond the non-inflatable area 22 along body portion 12. Further, two sets of four rows of apertures 26 and 28 sandwich the non-inflatable area 22. The two rows of the two sets of apertures furthest away from non-inflatable area 22, namely rows 26a and 28a, have more apertures than the respective three rows of apertures that are closer to the non-inflatable body area 22. There are also a plurality of apertures, namely the eight rows of apertures 30, provided longitudinally at the end of non-inflated area 22 that meets foot portion 14. The output of air from the rows of apertures 26, 28 and 30 form an envelope of heated air to warm the body of the patient, when the patient is placed onto upper sheet 4 of the blanket, with his body resting mainly on the non-inflatable body area 22, per shown in FIG. 4.

At the head portion 10 there is a cutout or opening 32, which is defined by a non-ending seal 34 having a width that is wider than the other non-ending seals in the blanket. Opening 32 may be considered to be a part of the head area of the head portion 10 whereon the patient's head rests. The patient may lie on the blanket with his head facing up or with his head facing down toward opening 32. If the patient were to lie face down on the blanket, he may be intubated with an air tube through opening 32 to assist his breathing. As shown, a plurality of apertures at the upper sheet 4, collectively designated 36, are provided at the upper left side of the head area proximate to opening 32 to output heated air to warm the head of the patient. Additional sets of apertures 38a and 38b are provided at the upper sheet 4 at the head area of the blanket closer to the neck of the patient.

Foot portion 14, and the lower part of body portion 12, have a number of spot seals 40 that bond the upper sheet 4 and the lower sheet 6 together to prevent that portion of the blanket from ballooning. Also, a plurality of apertures, designated by reference numbers 42a, 42b and 42c, are provided at foot portion 14. These apertures draw the heated air to the foot portion and in effect establish a drop in air pressure at the foot portion 14 to thereby better circulate or distribute the heated air throughout the blanket. As a result, the patient is warmed more efficiently. This enhanced air distribution takes place when heated air is input into the blanket via inlet port 44a located at the peripheral edge as shown at the head portion 10 of the blanket. Another inlet port 44b is provided at the peripheral edge at the foot portion 14 of the blanket. In operation, only one of the inlet ports is used. Details of the inlet ports are disclosed in U.S. Pat. No. 7,658,756, also assigned to the assignee of the instant application. The disclosure of the '756 patent is incorporated by reference herein.

With reference to the plan view of blanket 2 shown in FIG. 1, it can readily be seen that the body portion 12, generally indicated to be within side ends 12a and 12b, is substantially shaped in the form of a rectangle with a given width and a length defined by the opposite side ends 12a and 12b, which may be referenced by the dotted base lines 12a1 and 12b1, respectively. The head portion 10 is shown to taper in a decreasing manner from side end 12a of body portion 12 to head end 10a, so that the width of the blanket at the head end 10, designed 10a1, is smaller than the width of the body portion, represented for example by the width of side end 12a. The same is true with respect to the foot portion 14 where the two longitudinal peripheral sides of foot portion 14 extend in a similarly decreasing manner from side end 12b of body portion 12 to foot end 14a. As a consequence, the width 14a1 at the foot end 14a of the foot portion 14 is smaller than the width of the body portion exemplified for by side end 12b. Thus configured, each of head portion 10 and foot portion 14 has a shape in the form of an isosceles trapezoid—as side end 12a and head end 10a of the head portion 10 are in parallel, side end 12b and foot end 14a of the foot portion 14 are in parallel, and the tapered sides of each of the head and foot portions have equal lengths.

There are attached to the underside of the blanket, designated 6b in FIG. 2, two tuck flaps 46a and 46b. Tuck flaps 46a and 46b have respective longitudinal edges 46a1 and 46b1 that are fixedly attached the underside 6b of the blanket, so that they may freely hang per shown by respective dotted outlines 46a' and 46b' in FIG. 2. For ease of shipping and prior to use, the side edges for each of the tuck flaps 46a and 46b that are orthogonal to the longitudinal edges 46a1 and 46b1 (46a2 and 46a3 for tuck flap 46a; 46b2 and 46b3 for tuck flap 46b) may be removably attached to the underside of the blanket by for example two-sided tapes.

FIG. 2 shows the cross-sectional view 2-2 of FIG. 1, and in particular shows the blanket inflated with the top sheet 4 having two inflated channels 27 and 29 sandwiching the non-inflated area 22 of body portion 12. The two outside flow channels 48a and 48b are also shown. Each of the channels 27, 29, 48a and 48b has a plurality of apertures for outputting heated air to the patient when the blanket is inflated. The outputting of heated air to warm the patient is indicated by the exemplar directional arrows 50a and 50b from flow channels 27 and 29, respectively.

Figure 3:
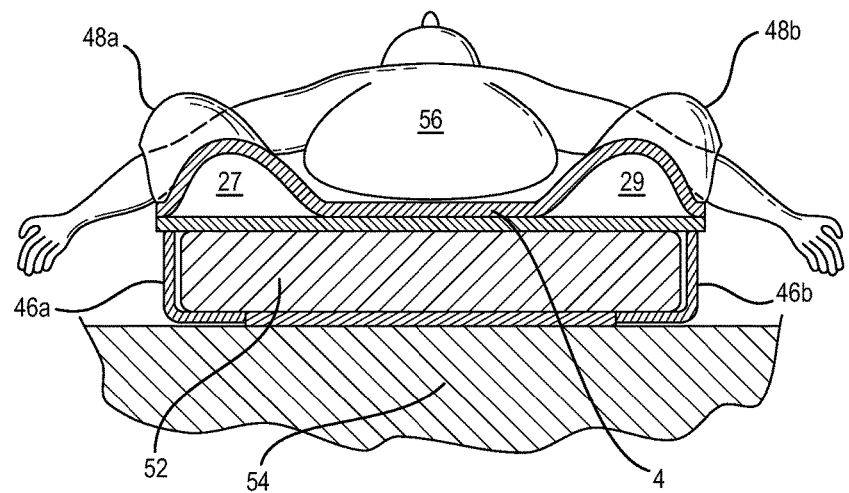
FIG. 3 is a cross-sectional view of the blanket with a patient lying thereon.

FIG. 3 is a cross-sectional view of the blanket shown lying on a support, for example a mattress 52, which in turn lies on another support, for example an operating table 54. Tuck flaps 46a and 46b may be used to secure the blanket to mattress 52 per shown. A patient 56 is shown to be positioned onto the upper sheet 4 of the blanket and has his arms extending through the elongate openings 18a and 18b. See also FIG. 4.

Figure 4:
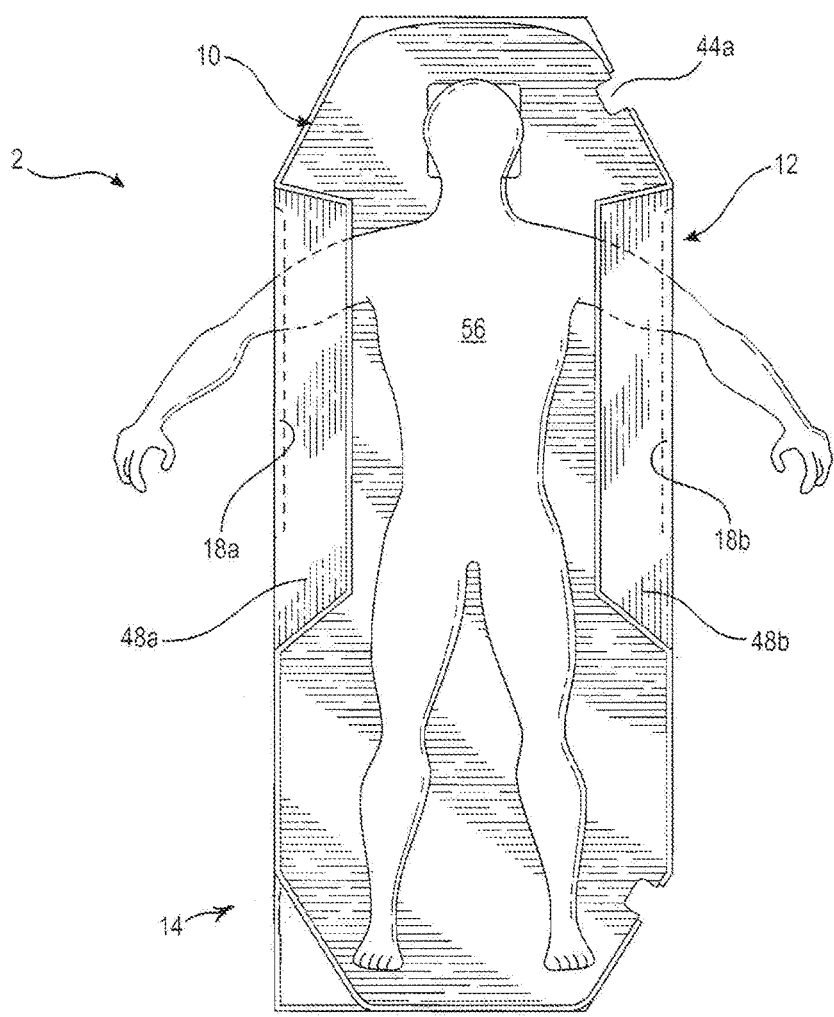
FIG. 4 is a plan view of the blanket with a patient lying thereon.

As shown in FIG. 4, with channels 48a and 48b folded inwardly toward the center of the blanket and the arms of the patient 56 extending through the elongate openings 18a and 18b, the blanket 2 is firmly secured to the patient. Although FIG. 4 shows the patient to be facing upwards away from the blanket, there are instances where the patient may be placed onto the blanket face down with his face facing the opening 32 at the head portion 10. The patient then may be intubated with an air supply tube to assist his breathing. To ensure that the head of the patient does not fall through the opening 32, the dimension of opening 32 may be limited to the range of 6-9 inches (15-23 cm), and preferably between 7-8 inches (18-20 cm).

The invention claimed is:

1. An underbody blanket, comprising:
an air impermeable upper sheet and an air impermeable lower sheet bonded to each other at their respective peripheries to form an inflatable structure having a periphery defining therewithin a head portion, a body portion and a foot portion, each of the head and foot portions having longitudinal sides that have the same length that narrow in a straight tapered manner toward each other from opposite sides of the body portion to respective head and foot ends of the structure so that each of the head and foot portions has same length tapered sides;
two elongate openings each having a given width and a given length formed by a corresponding non-ending seal that encircles the each opening, each non-ending seal having a length extending longitudinally along substantially the length of the body portion, the elongate openings sandwiching a non-inflatable area of the body portion whereon the body of a patient rests when the patient is positioned onto the upper sheet of the blanket;
at least one inlet port provided at the structure; and
apertures formed in the upper sheet to enable heated air input via the inlet port to inflate the structure to escape, respective rows of apertures provided proximately along each longitudinal side of the non-inflatable body area positioned to face the patient when the structure is inflated so that the heated air output from those respective rows of apertures is directed to the patient, each of the respective rows of apertures positioned between the non-inflatable body area and a corresponding one of the elongate openings.

2. The blanket of claim 1, wherein the head portion of the structure comprises a head area including another opening defined by another non-ending seal.

3. The blanket of claim 2, further comprising a plurality of apertures at the upper sheet located proximately to at least one portion of the opening at the head area.

4. The blanket of claim 1, wherein apertures are provided at the foot portion to establish a pressure drop thereat to facilitate a more evenly distributed flow of the heated air in the structure.

5. The blanket of claim 1, further comprising at least one flap having at least one edge fixedly attached to the underside of the lower sheet, the flap usable to secure the blanket to a surface of a support for the blanket when not held intimately to the underside of the structure.

6. The blanket of claim 1, further comprising two flaps, each of the flaps having a longitudinal edge fixedly attached to the underside of the lower sheet adjacent to the side of a corresponding one of the elongate openings toward the non-inflatable body area of the body portion.

7. The blanket of claim 1, wherein the non-ending seal of each of the elongate openings is formed with a sealed cavity at each of its longitudinal ends to provide strain relief for the each elongate opening, respective sets of multiple apertures formed on the upper sheet between each of the elongate openings and the periphery of the blanket.

8. The blanket of claim 1, wherein there are two inlet ports provided at the blanket, one of the inlet ports provided at the peripheral edge at the head portion of the structure and other of the inlet ports provided at the peripheral edge at the foot portion of the structure, either the one and other inlet ports being usable to input air into the blanket.

\* \* \* \* \*